United States Patent
Anderson et al.

(10) Patent No.: US 7,044,959 B2
(45) Date of Patent: May 16, 2006

(54) METHOD AND APPARATUS FOR HAIR GROWTH MANAGEMENT

(75) Inventors: R. Rox Anderson, Lexington, MA (US); Gregory B. Altshuler, Wilmington, MA (US); Dieter Manstein, Boston, MA (US); Ilya Yaroslavsky, Wilmington, MA (US); Michael Smotrich, Andover, MA (US)

(73) Assignees: Palomar Medical Technologies, Inc., Burlington, MA (US); The General Hospital Corporation, Boston, MA (US)

( * ) Notice: Subject to any disclaimer, the term of this patent is extended or adjusted under 35 U.S.C. 154(b) by 135 days.

(21) Appl. No.: 10/346,749

(22) Filed: Mar. 12, 2003

(65) Prior Publication Data

US 2004/0034319 A1    Feb. 19, 2004

Related U.S. Application Data

(60) Provisional application No. 60/363,871, filed on Mar. 12, 2002.

(51) Int. Cl.
*A61N 5/06* (2006.01)
*A61B 18/18* (2006.01)

(52) U.S. Cl. .............................. 607/88; 128/898; 606/9

(58) Field of Classification Search ................ 128/898; 606/9; 607/88–91
See application file for complete search history.

(56) References Cited

U.S. PATENT DOCUMENTS

| | | | |
|---|---|---|---|
| 3,327,712 A | 6/1967 | Kaufman et al. |
| 3,527,932 A | 9/1970 | Thomas |
| 3,538,919 A | 11/1970 | Meyer |
| 3,622,743 A | 11/1971 | Muncheryan |
| 3,693,623 A | 9/1972 | Harte et al. |
| 3,818,914 A | 6/1974 | Bender |
| 3,834,391 A | 9/1974 | Block |
| 3,900,034 A | 8/1975 | Katz et al. |
| 4,233,493 A | 11/1980 | Nath |
| 4,273,109 A | 6/1981 | Enderby |
| 4,316,467 A | 2/1982 | Muckerheide |
| 4,388,924 A | 6/1983 | Weissman et al. |
| 4,461,294 A | 7/1984 | Baron |
| 4,539,987 A | 9/1985 | Nath et al. |

(Continued)

FOREIGN PATENT DOCUMENTS

EP    0142671 A1    5/1985

(Continued)

OTHER PUBLICATIONS

Altshuler et al., "Acoustic response of hard dental tissues to pulsed laser action," SPIE, vol. 2080, Dental Application of Lasers, pp. 97-103, 1993.

(Continued)

*Primary Examiner*—Roy D Gibson
*Assistant Examiner*—Henry M Johnson, III
(74) *Attorney, Agent, or Firm*—Thomas J. Engellenner; Deborah A. Miller; Nutter McClennen & Fish LLP

(57) ABSTRACT

A method and apparatus are provided for hair growth management by applying low energy optical radiation to a treatment area of a patient's skin, which radiation is sufficient to at least traumatize a matrix portion of each follicle being treated, but not to cause either necrosis of most of each said follicle or immediate gross alteration of any hair shaft therein. The treatments are preferably performed a plurality of times at selected time intervals to achieve a desired level of hair growth management.

12 Claims, 4 Drawing Sheets

U.S. PATENT DOCUMENTS

| | | |
|---|---|---|
| 4,608,978 A | 9/1986 | Rohr |
| 4,617,926 A | 10/1986 | Sutton |
| 4,695,697 A | 9/1987 | Kosa |
| 4,718,416 A | 1/1988 | Nanaumi |
| 4,733,660 A | 3/1988 | Itzkan |
| 4,747,660 A | 5/1988 | Nishioka et al. |
| 4,819,669 A | 4/1989 | Politzer |
| 4,832,024 A | 5/1989 | Boussignac et al. |
| 4,860,172 A | 8/1989 | Schlager et al. |
| 4,860,744 A | 8/1989 | Johnson et al. |
| 4,917,084 A | 4/1990 | Sinofsky |
| 4,926,227 A | 5/1990 | Jensen |
| 4,945,239 A | 7/1990 | Wist et al. |
| 5,000,752 A | 3/1991 | Hoskin et al. |
| 5,057,104 A | 10/1991 | Chess |
| 5,059,192 A | 10/1991 | Zaias |
| 5,065,515 A | 11/1991 | Iderosa |
| 5,071,417 A | 12/1991 | Sinofsky |
| 5,108,388 A | 4/1992 | Trokel |
| 5,137,530 A | 8/1992 | Sand |
| 5,140,984 A | 8/1992 | Dew et al. |
| 5,178,617 A | 1/1993 | Kuizenga et al. |
| 5,182,557 A | 1/1993 | Lang |
| 5,182,857 A | 2/1993 | Simon |
| 5,196,004 A | 3/1993 | Sinofsky |
| 5,207,671 A | 5/1993 | Franken et al. |
| 5,225,926 A | 7/1993 | Cuomo et al. |
| 5,226,907 A | 7/1993 | Tankovich |
| 5,282,797 A | 2/1994 | Chess |
| 5,300,097 A | 4/1994 | Lerner et al. |
| 5,304,170 A | 4/1994 | Green |
| 5,306,274 A | 4/1994 | Long |
| 5,320,618 A | 6/1994 | Gustafsson |
| 5,334,191 A | 8/1994 | Poppas et al. |
| 5,334,193 A | 8/1994 | Nardella |
| 5,344,418 A | 9/1994 | Ghaffari |
| 5,344,434 A | 9/1994 | Talmore |
| 5,348,551 A | 9/1994 | Spears et al. |
| 5,350,376 A | 9/1994 | Brown |
| 5,380,317 A | 1/1995 | Everett et al. |
| 5,403,306 A | 4/1995 | Edwards et al. |
| 5,405,368 A | 4/1995 | Eckhouse |
| 5,415,654 A | 5/1995 | Daikuzono |
| 5,425,728 A | 6/1995 | Tankovich |
| 5,474,549 A | 12/1995 | Ortiz et al. |
| 5,486,172 A | 1/1996 | Chess |
| 5,505,726 A | 4/1996 | Meserol |
| 5,505,727 A | 4/1996 | Keller |
| 5,519,534 A | 5/1996 | Smith et al. |
| 5,522,813 A | 6/1996 | Trelles |
| 5,531,739 A | 7/1996 | Trelles |
| 5,558,667 A | 9/1996 | Yarborough et al. |
| 5,578,866 A | 11/1996 | DePoorter et al. |
| 5,595,568 A | 1/1997 | Anderson et al. |
| 5,616,140 A | 4/1997 | Prescott |
| 5,620,478 A | 4/1997 | Eckhouse |
| 5,626,631 A | 5/1997 | Eckhouse |
| 5,630,811 A | 5/1997 | Miller |
| 5,649,972 A | 7/1997 | Hochstein |
| 5,655,547 A | 8/1997 | Karni |
| 5,658,323 A | 8/1997 | Miller |
| 5,662,643 A | 9/1997 | Kung et al. |
| 5,662,644 A | 9/1997 | Swor |
| 5,683,380 A | 11/1997 | Eckhouse et al. |
| 5,698,866 A | 12/1997 | Doiron et al. |
| 5,707,403 A | 1/1998 | Grove et al. |
| 5,720,772 A | 2/1998 | Eckhouse |
| 5,735,844 A | 4/1998 | Anderson et al. |
| 5,735,884 A | 4/1998 | Thompson et al. |
| 5,743,901 A | 4/1998 | Grove et al. |
| 5,755,751 A | 5/1998 | Eckhouse |
| 5,759,200 A | 6/1998 | Azar |
| 5,782,249 A | 7/1998 | Weber et al. |
| 5,810,801 A | 9/1998 | Anderson et al. |
| 5,817,089 A | 10/1998 | Tankovich et al. |
| 5,820,625 A | 10/1998 | Izawa et al. |
| 5,820,626 A | 10/1998 | Baumgardner |
| 5,824,023 A | 10/1998 | Anderson |
| 5,828,803 A | 10/1998 | Eckhouse |
| 5,830,208 A | 11/1998 | Muller |
| 5,836,999 A | 11/1998 | Eckhouse et al. |
| 5,849,029 A | 12/1998 | Eckhouse et al. |
| 5,853,407 A | 12/1998 | Miller |
| 5,871,480 A | 2/1999 | Tankovich |
| 5,885,211 A | 3/1999 | Eppstein et al. |
| 5,885,273 A | 3/1999 | Eckhouse et al. |
| 5,885,274 A | 3/1999 | Fullmer et al. |
| 5,916,211 A * | 6/1999 | Quon et al. ............ 606/9 |
| 5,944,748 A | 8/1999 | Mager et al. |
| 5,948,011 A | 9/1999 | Knowlton |
| 5,954,710 A | 9/1999 | Paolini et al. |
| 5,964,749 A | 10/1999 | Eckhouse et al. |
| 5,968,033 A | 10/1999 | Fuller |
| 5,968,034 A | 10/1999 | Fullmer et al. |
| 6,015,404 A | 1/2000 | Altshuler et al. |
| 6,027,495 A | 2/2000 | Miller |
| RE36,634 E | 3/2000 | Ghaffari |
| 6,050,990 A | 4/2000 | Tankovich et al. |
| 6,056,738 A | 5/2000 | Marchitto et al. |
| 6,059,820 A | 5/2000 | Baronov |
| 6,074,382 A | 6/2000 | Asah et al. |
| 6,080,146 A | 6/2000 | Altshuler et al. |
| 6,096,029 A | 8/2000 | O'Donnell, Jr. |
| 6,096,209 A | 8/2000 | O'Brien et al. |
| 6,104,959 A | 8/2000 | Spertell |
| 6,120,497 A | 9/2000 | Anderson |
| 6,149,644 A | 11/2000 | Xie |
| 6,174,325 B1 | 1/2001 | Eckhouse |
| 6,187,001 B1 * | 2/2001 | Azar et al. ............ 606/9 |
| 6,197,020 B1 | 3/2001 | O'Donnell |
| 6,228,075 B1 | 5/2001 | Furumoto |
| 6,235,016 B1 | 5/2001 | Stewart |
| 6,273,884 B1 | 8/2001 | Altshuler et al. |
| 6,273,885 B1 | 8/2001 | Koop et al. |
| 6,280,438 B1 | 8/2001 | Eckhouse et al. |
| 6,283,956 B1 | 9/2001 | McDaniel |
| 6,306,130 B1 | 10/2001 | Anderson et al. |
| 6,354,370 B1 | 3/2002 | Miller et al. |
| 6,475,211 B1 | 11/2002 | Chess et al. |
| 6,508,813 B1 | 1/2003 | Altshuler et al. |
| 6,511,475 B1 | 1/2003 | Altshuler et al. |
| 6,517,532 B1 | 2/2003 | Altshuler et al. |
| 6,663,659 B1 * | 12/2003 | McDaniel ............ 606/3 |
| 6,808,532 B1 | 10/2004 | Andersen et al. |
| 2002/0005475 A1 | 1/2002 | Zenzie |
| 2002/0091377 A1 | 7/2002 | Anderson et al. |
| 2002/0128635 A1 | 9/2002 | Altshuler et al. |
| 2002/0161357 A1 | 10/2002 | Anderson et al. |
| 2002/0173780 A1 | 11/2002 | Altshuler et al. |
| 2003/0004499 A1 * | 1/2003 | McDaniel ............ 606/3 |
| 2003/0023283 A1 | 1/2003 | McDaniel |
| 2003/0032950 A1 | 2/2003 | Altshuler et al. |
| 2003/0055414 A1 | 3/2003 | Altshuler et al. |
| 2003/0065314 A1 | 4/2003 | Altshuler et al. |

FOREIGN PATENT DOCUMENTS

| | | |
|---|---|---|
| EP | 0565331 A2 | 10/1993 |
| EP | 0598984 A1 | 6/1994 |
| EP | 0724894 A2 | 8/1996 |
| EP | 0726083 A2 | 8/1996 |
| EP | 0736308 A2 | 10/1996 |
| EP | 0755698 A2 | 1/1997 |
| EP | 0763371 A2 | 3/1997 |

| | | | |
|---|---|---|---|
| EP | 0765673 A2 | 4/1997 |
| EP | 0765674 A2 | 4/1997 |
| EP | 0783904 A2 | 7/1997 |
| GB | 2044908 A | 10/1980 |
| GB | 2123287 A | 2/1984 |
| GB | 2360946 A | 10/2001 |
| RU | 2089126 C1 | 10/1997 |
| RU | 2089127 C1 | 10/1997 |
| RU | 2096051 C1 | 11/1997 |
| RU | 2122848 C1 | 10/1998 |
| WO | WO 86/027837 A1 | 5/1986 |
| WO | WO 90/00420 A1 | 1/1990 |
| WO | WO 91/13652 A1 | 9/1991 |
| WO | WO 92/16338 A1 | 10/1992 |
| WO | WO 92/19165 A1 | 11/1992 |
| WO | WO 93/05920 A1 | 4/1993 |
| WO | WO 95/15725 A1 | 6/1995 |
| WO | WO 95/32441 A1 | 11/1995 |
| WO | WO 96/23447 A1 | 8/1996 |
| WO | WO 96/25979 A1 | 8/1996 |
| WO | WO 97/13458 A1 | 4/1997 |
| WO | WO 98/04317 A1 | 2/1998 |
| WO | WO 98/24507 A1 | 6/1998 |
| WO | WO 98/51235 A1 | 11/1998 |
| WO | WO 98/52481 A1 | 11/1998 |
| WO | WO 99/27997 A1 | 6/1999 |
| WO | WO 99/29243 A1 | 6/1999 |
| WO | WO 99/38569 A2 | 8/1999 |
| WO | WO 99/38569 A3 | 8/1999 |
| WO | WO 99/46005 A1 | 9/1999 |
| WO | WO 99/49937 A1 | 10/1999 |
| WO | WO 00/03257 A1 | 1/2000 |
| WO | WO 00/44294 A1 | 8/2000 |
| WO | WO 00/71045 A1 | 11/2000 |
| WO | WO 00/74781 A1 | 12/2000 |
| WO | WO 00/78242 A1 | 12/2000 |
| WO | WO 01/03257 A1 | 1/2001 |
| WO | WO 01/34048 A1 | 5/2001 |
| WO | WO 01/42671 A1 | 6/2001 |
| WO | WO 01/54606 A1 | 8/2001 |
| WO | WO 01/78830 A2 | 10/2001 |
| WO | WO 02/53050 A1 | 7/2002 |
| WO | WO 02/069825 A2 | 9/2002 |
| WO | WO 02/094116 A1 | 11/2002 |

OTHER PUBLICATIONS

Alsthuler et al., "Extended theory of selective photothermolysis," Lasers in Surgery and Medicine, vol. 29, pp. 416-432, 2001.
Amy et al., "Selective mitochondrial damage by a ruby laser microbeam: An electron microscopic study," Science, vol. 15, pp. 756-758, Nov. 1965.
Anderson et al., "The optics of human skin," Journal of Investigative Dermatology, vol. 77, No. 1, pp. 13-19, 1981.
Anderson et al., "Selective photothermolysis: Precise Microsurgery by selective absorption of pulsed radiation," Science, vol. 220, pp. 524-527, Apr. 1983.
Belikov et al., "Identification of enamel and dentine under tooth laser treatment," SPIE vol. 2623, Progress in Biomedical Optics Europe Series, Proceedings of Medical Applications of Lasers III, pp. 109-116. Sep. 1995.
Dover et al., "Pigmented guinea pig skin irrdiated with Q-switched ruby laser pulses," Arch Dermatol, vol. 125, pp. 43-49, Jan. 1989.
Finkelstein et al., "Epilation of hair-bearing urethral grafts using the neodymium:yag surgical laser," Journal of Urology, vol. 146, pp. 840-842, Sep. 1991.
L. Goldman, Biomedical Aspects of the Laser, Springer-Verlag New York Inc., publishers, Chapts. 1, 2, & 23, 1967.
L. Goldman, "Dermatologic manigestations of laser radiation," Proceedings of the First Annual Conference on Biologic Effects of Laser Radiation, Federation of American Societies for Experimental Biology, Supp. No. 14, pp. S-92-S-93, Jan.-Feb. 1965.
L. Goldman, "Effects of new laser systems on the skin," Arch Dermatol., vol. 108, pp. 385-390, Sep. 1973.
L. Goldman, "Laser surgery for skin cancer, " New York State Journal of Medicine, pp. 1897-1900, Oct. 1977.
L. Goldman, "Surgery by laser for malignant melanoma," J. Dermatol. Surg. Oncol., vol., 5, No. 2, pp. 141-144, Feb. 1979.
L. Goldman, "The skin," Arch Environ Health, vol. 18, pp. 434-436, Mar. 1969.
L. Goldman & D.F. Richfield, "The effect of repeated exposures to laser beams," Acta derm.-vernereol., vol. 44, pp. 264-268, 1964.
L. Goldman & R.J. Rockwell, "Laser action at the cellular level," JAMA, vol. 198, No. 6, pp. 641-644, Nov. 1966.
L. Goldman & R.G. Wilson, "Treatment of basal cell epithelioma by laser radiation," JAMA, vol. 189, No. 10, pp. 773-775.
L. Goldman et al., "The biomedical aspects of lasers," JAMA, vol. 188, No. 3, pp. 302-306, Apr. 1964.
L. Goldman et al., "Effect of the laser beam on the skin, Preliminary report" Journal of Investigative Dermatology, vol. 40, pp. 121-122, 1963.
L. Goldman et al., "Effect of the laser beam on the skin, III. Exposure of cytological preparations," Journal of Investigative Dermatology, vol. 42, pp. 247-251, 1964.
L. Goldman et al., "Impact of the laser on nevi and melanomas," Archives of Dermatology, vol. 90, pp. 71-75, Jul. 1964.
L. Goldman et al., "Laser treatment of tattoos, A preliminary survey of three year's clinical experience," JAMA, vol. 201, No. 11, pp. 841-844, Sep. 1967.
L. Goldman et al., "Long-term laser exposure of a senile freckle," ArchEnviron Health, vol. 22, pp. 401-403, Mar. 1971.
L. Goldman et al., "Pathology, Pathology of the effect of the laser beam on the skin," Nature, vol. 197, No. 4870, pp. 912-914, Mar. 1963.
L. Goldman et al., "Preliminary investigation of fat embolization from pulsed ruby laser impacts of bone," Nature, vol. 221, pp. 361-363, Jan. 1969.
L. Goldman et al., "Radiation from a Q-switched ruby laser, Effect of repeated impacts of power output of 10 megawatts on a tattoo of man," Journal of Investigative Deratology, vol. 44, pp. 69-71, 1965.
L. Goldman et al., "Replica microscopy and scanning electron microscopy of laser impacts on the skin," Journal of Investigative Dermatology, vol. 52, No. 1, pp. 18-24, 1969.
Grossman et al., "Damage to hair follicles by normal-mode ruby laser pulses," Journal of he American Academy of Dermatology, vol. 35, No. 6, pp. 889-894, Dec. 1996.
Klein et al., "Biological effects of laser radiation 1., " Northeast Electronics Research and Engineering Meeting, NEREM Record, IEEE catalogue No. F-60, pp. 108-109, 1965.
Kuhns et al., "Laser injury in skin," Laboratory Investigation, vol. 17,No. 1, pp. 1-13, Jul. 1967.
Kuhns et al., "Biological effects of laser radiation II Effects of laser irradiation on the skin," NEREM Record, pp. 152-153, 1965.

Margolis et al., "Visible action spectrum for melanin-specific selective photothermolysis," Lasers in Surgery and Medicine, vol. 9, pp. 389-397, 1989.

J.A. Parrish, "Selective thermal effects with pulsed irradiation from lasers: From organ to organelle," Journal of Investigative Dermatology, vol. 80, No. 6 Supplement, pp. 75s-80s, 1983.

Polla et al., "Melanosomes are a primary target of Q-switched ruby laser irradiation in guinea pig skin," Journal of Investigative Dermatolgy, vol. 89, No. 3, pp. 281-286, Sep. 1987.

Riggle et al., "Laser effects on normal and tumor tissue," Laser Applications in Medicine and Biology, vol. 1, M.L. Wolbarsht, editor, Plenum Press, publishers, chapter 3, pp. 35-65, 1971.

Shimbashi et al., "Ruby laser treatment of pigmented skin lesions," Aesth. Plast. Surg., vol. 19, pp. 225-229, 1995.

Stratton et al., "Biological Effects of Laser Radiation II: ESR Studies of Melanin Containing Tissues after Laser Irradiation," Northeast Electronics Research and Engineering Meeting—NEREM Record, IEEE Catalogue No. F-60, pp. 150-151, Nov. 1965.

Taylor et al., "Treatment of tattoos by Q-switched ruby laser," Arch. Dermatol. vol. 126, pp. 893-899, Jul. 1990.

V.V. Tuchin, "Laser light scattering in biomedical diagnostics and therapy," Journal of Laser Applications, vol. 5, No. 2-3, pp. 43-60, 1993.

Watanabe et al, "Comparative studies of femtosecond laser pulses on selective pigmented cell injury in skin," Photochemistry and Photobiology, vol. 53, No. 6, pp. 757-762, 1991.

Welch et al., "Evaluation of cooling techniques for the protection of the epidermis during HD-yag laser irradiation of the skin," Neodymium-Yag Laser in Medicine and Surgery, Elsevier Science Publishing Co., publisher, pp. 195-204, 1983.

Yules et al., "The effect of Q-switched ruby laser radiation on dermal tattoo pigment in man," Arch Surg, vol. 95, pp. 179-180, Aug. 1967.

Zeitler et al., "Laser Characteristics that Might be Useful in Biology," *Laser Applications in Medicine and Biology*, 1:1-16, 1971.

Abstracts Nos. 17-19, Lasers in Surgery and Medicine, ASLMS, Supplement 13, 2001.

Abstracts Nos. 219-223, ASLMS.

* cited by examiner

METHOD AND APPARATUS FOR HAIR GROWTH MANAGEMENT

RELATED APPLICATIONS

This application claims the benefit under 35 U.S.C. 119(e) of U.S. Provisional Patent Application No. 60/363,871, filed Mar. 12, 2002, entitled "Method and Apparatus for Hair Growth Control," by R. Anderson, et al., incorporated herein by reference in its entirety.

FIELD OF THE INVENTION

This invention relates to hair growth management and more particularly to a method and apparatus for managing or controlling hair growth without causing immediate histological alterations of the hair follicles which are detectable by routine light microscopy or gross alteration or destruction of the hair shaft or to at least a portion of the hair follicle.

BACKGROUND OF THE INVENTION

While there are some areas of a person's body where it is desired to permanently remove hair, for example facial or leg hair on a woman, frequently, for the hair indicated above as well as for undesired hair on other parts on both a man's and a woman's body, a lower level of hair growth management may be all that is desired. Hair growth management may involve temporary, for example for several weeks, or permanent cessation of hair growth; temporarily or permanently changing, either increasing or decreasing, the hair growth rate; and/or temporarily or permanently changing selected characteristics of the hair shaft including, but not limited to, changing hair shaft diameter, shape, pigmentation, and mechanical properties such as elasticity and bend/curl. Hair growth management may involve removal of the hair shaft, destruction of the hair shaft, and/or changes in the hair follicle structure. Most current techniques for hair management are techniques for hair removal by applying radiation to the patient's skin, generally optical radiation, in relatively high radiation doses sufficient to denature protein tissue of the hair follicle, and thus to generally cause necrosis of the follicle. The energy applied in such techniques also generally results in immediate destruction or significant alterations of the hair shaft. However, the application of such high energy to a patient's skin can also cause damage to the patient's epidermis, particularly for darker skinned individuals, can in some instances cause dermal damage or scarring and, even with protective procedures such as cooling of the skin before and during treatment, can result in various levels of discomfort and pain to the patient being treated. This has resulted in a requirement that such procedures be performed by a dermatologist or other qualified physician, or at least under the supervision of such a physician. The high power/energy devices used for performing such procedures are also relatively expensive. The combination of relatively expensive equipment with the need for the procedures to be performed by high priced, highly trained personnel has resulted in such hair removal procedures being relatively expensive, significantly limiting the availability of such procedures to the public, and such availability has been further limited by difficulties in treating dark skinned individuals.

A need therefore exists for procedures to manage hair growth for a selected time periods, for example several days to a month for facial hair (men's beard), and several weeks or more (for example, months) for other body areas, which can safely be performed on individuals with all types of skin, and which is sufficiently low powered and safe so that it can be performed by non-medical personnel, for example barbers, beauticians and spa operators, or even in the home by the person on whom the procedure is being performed. Such procedures should result in little or no pain or discomfort to the person on whom the treatment is being performed, should result in no visible alteration to such person's skin or other side effects, should be very low cost for a single treatment and should be repeatable at selected intervals to achieve a desired level of hair growth management. A technique for achieving these objectives does not currently exist.

SUMMARY OF THE INVENTION

In accordance with the above, this invention provides a method for hair growth management in a treatment area of a patient's skin which involves applying optical radiation to hair follicles in the treatment area of a wavelength, power density and duration sufficient to at least traumatize a matrix portion of at least selected follicles in the treatment area, but not sufficient to cause either necrosis of most of each said follicle or immediate gross alteration of any hair shaft therein. A basement membrane of the matrix located between the matrix and papilla of the follicle may be also traumatized. The matrix is preferably heated to a temperature in the range indicated in FIG. 2, but at least most of each treated follicle is at a temperature below this range. The ranges for wavelength, power density and duration are substantially within the ranges provided in Table 1, depending on the color of the hair shafts in the treatment area. The treatment method is preferably repeated at selected time intervals, which intervals may be from one day to eight weeks, but are preferably one week to six weeks. Loose hairs may be stripped from the treatment area at a time approximately one to two weeks after the method is performed, tape for example being used to remove the loose hairs. For some embodiments, optical radiation is scanned over the treatment area at a speed generally within the ranges indicated in Table 3, the power densities of radiation from the source used depending on the wavelength of the source, the width of the scanning beam and the scanning speed, generally as indicated in Table 3. Where the radiation is scanned, the optical radiation source used may be a continuous wave (CW) source. At least a selected portion of the treatment area may also be irradiated a plurality of times during a treatment.

The method of hair growth management may also involve applying optical radiation to hair follicles in a treatment area of a wavelength, power density and duration sufficient to drive the follicles into a transitional growth arrested state, but not to cause either necrosis of most of each said follicle or immediate gross alteration of any hair shaft therein. The treatment of this method may also be repeated at selected time intervals.

The invention also involves apparatus for hair growth management in a treatment area of a patient's skin which includes a source of optical radiation; and a mechanism for applying the radiation to the treatment area; the source being of a wavelength, power density and duration sufficient when applied to hair follicles in said treatment area to at least traumatize a matrix portion of at least selected follicles in the treatment area, but not sufficient to cause either necrosis of most of each said follicle or immediate gross alteration of any hair shaft therein. Ranges for wavelengths, power density and duration of the source are substantially within the ranges provided in Table 1, depending on the color of hair shafts in the treatment area.

The foregoing and other objects, features and advantages of the invention will be apparent from the following more particular description of preferred embodiments of the invention as illustrated in the accompanying drawings, the same or related reference numerals being used for common elements in the various figures.

DESCRIPTION OF INVENTION

General Concepts

Figure 1:
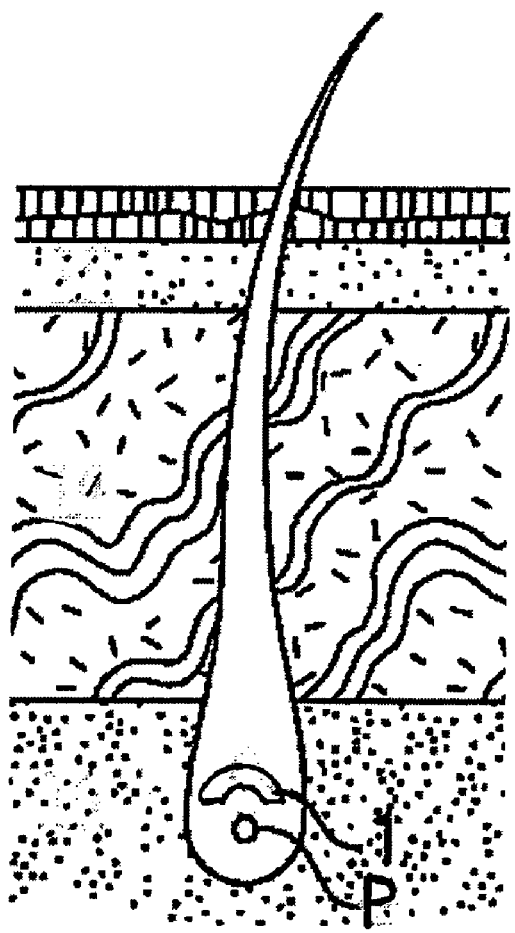
FIG. 1 is an illustration of an anagen hair follicle.

As indicated above, hair removal using optical radiation as currently practiced has as its objective, the permanent removal of the hair shaft and associated hair follicle. This procedure is similar in objective to the practice of electrolysis. In both cases, the hair shaft is removed and the follicle damaged. In particular, the requirement for permanency is satisfied in both electrolysis and optical hair removal by damaging the epithelium of the follicle, causing the formation of scar tissue, resulting in the permanent disablement of the hair follicle. Permanency may also be attempted by destruction of the stem cells responsible for the perpetuation of the hair growth cycle, located in the bulge region of the folliculo-sebaceous unit.

Based on extensive clinical study of laser/light mediated hair growth management in humans, it has been clearly established as a power density, pulse width and energy density related process. Provided that the laser, light-emitting diode (LED), lamp or other optical energy source radiates at a wavelength consistent with absorption by the hair follicle system, power densities above a certain level, which level is dependent on a number of factors to be discussed later, can result in permanent hair loss. It has been observed that for lower power densities or fluences, it is possible to obtain changes in the nature of growing hair: hair may be lighter in color and thinner; hair growth may be slower and finally, hair may eventually fall out, causing temporary hair loss. However, certain other combinations of treatment parameters may, in fact, result in the opposite effect, i.e. increase of the hair growth rate as well as hair shaft diameter and pigmentation.

While light treatment of hair at power density levels below that required for permanent hair loss is not desirable as a dermatological tool in the rapid treatment of hirsutism, it is acceptable and, as indicated above, in many cases desirable, in the cosmetic treatment of hair. It may also be usable for extended term treatment of hirsutism.

The invention may generally be characterized as the discovery that an optical radiation treatment range, heretofore considered to be inadequate for the treatment of hirsutism and the establishment of permanent hair loss, is available and is valuable as a mechanism for the cosmetic treatment of hair. The invention specifically defines new treatment parameter ranges optimized in terms of safety and efficacy, which can be used in a non-medical environment to perform hair growth management. Operation within the conditions specified will allow operation of treatment devices in a self-treatment mode and/or by non-medical personnel. While some temporary benefits can be obtained from a single treatment employing the parameters of this invention, to achieve desired levels of hair growth management, it is normally necessary to perform multiple treatments at selected time intervals, which intervals may vary from approximately one day to eight weeks, with intervals of one to six weeks generally being preferred. The preferred treatment interval may vary with the patient being treated, the part of the patient's body being treated and other factors, and may increase as the number of treatments performed increases.

In considering possible mechanisms which may explain the performance of optical radiation devices in the cosmetic range, attention is drawn to the follicular matrix. The matrix, which is only found in growing or anagen hair follicles, represents the "engine" of the factory responsible for hair formation, hair coloring and hair growth. Matrix cells of a follicular bulb constitute a pool of undifferentiated cells whose metabolic activity is so intense that a complete cycle of those cells in follicles on a human scalp is only about 39 hours. The rapid rate of turnover of the matrix cells is greater than that of any normal tissue, with the possible exception of bone marrow. Matrix cells contiguous with a papilla adjacent the matrix proliferate especially rapidly. They power the movement of cells of a future hair toward the skin surface. As the distance of matrix cells from the papilla increases, the mitotic activity of the cells decreases.

Clearly, what is described is a rapidly growing cellular system, requiring optimum conditions for continued high performance. In particular, it is necessary that the entire matrix is available for the production of hair and access to the blood supply of the papilla so that the energy necessary for the metabolic process is not compromised. Therefore, trauma to the matrix or papilla, or a portion thereof, or any condition which interrupts or reduces access of the matrix to blood supply from the papilla, can limit or control the rate at which the matrix drives the hair production process; this may therefore be a key to managing hair growth. This control depends on how completely or to what extent the functioning of the matrix cells and/or the blood supply in the papilla is limited. In currently available light-based hair growth management systems, the objective is primarily permanent elimination of the hair, which in light of this discussion, means the complete destruction of the matrix and papilla. Fundamental to this invention is the limiting of destruction/perturbation of the follicle in general, and of the matrix, in particular, and to a lesser extent the papilla, to the extent needed to accomplish the objective of temporary hair growth management. This requirement of sufficient but limited damage/perturbation places this process in the regime in which subtle processes known to control the formation and destruction of cells operate. For example, actual management of matrix cell death may be controlled by an apoptotic action, which in turn is mediated by molecular regulators produced as a result of the light energy perturbation. The natural growth cycle of every hair follicle proceeds from an active growth state (anagen) in which the matrix and papilla are active, to an inactive state (telogen) in which the matrix is absent and the papilla is separated from the hair follicle. The transition between anagen and telogen states is called catagen, which is driven by apoptosis (programmed cell death) of the matrix and adjacent parts of the hair follicle epithelium. Because of this natural cycle, anagen hair follicles can be triggered into a catagen-like state by subtle thermal injury of the matrix and/or adjacent parts of the hair follicle epithelium. In the case of optical radiation mediated hair growth which operates on the principal of, for example, thermal perturbation or traumatization of matrix cells, papillary cells or the papillary blood supply, the characteristics of the perturbing optical source should have the correct wavelength content to be absorbed by chromophores in the matrix (melanocytes) and/or in the blood supply (hemoglobin). It is also necessary in some cases to optimize light pulse duration to ensure proper heat diffusion time between absorbing chromophores and targeted cells.

In the method of the present invention, the light treatment in people affects mostly anagen follicles. However, catagen and telogen follicles may also contribute to the resulting hair loss.

Regarding possible mechanisms for light treatment on an anagen follicle utilizing the method of the present invention, two hypotheses are consistent with the observed clinical pattern of hair growth reduction:

I. Light treatment induces premature or accelerated transition of the affected hair follicle from anagen into a dystrophic anagen or a telogen state through a transitional state similar to an altered or modified catagen state.

II. The affected follicle remains in an anagen or transitional growth arrested (TGA) state where the proliferation and melanogenesis rates are reduced, the hair growth may prematurely stop.

Regardless of the dominant mechanism, the hair in the follicle sheds after about a week to two weeks or may be easily removed by passing a tape over the hairs. When the follicle is in the light-induced catagen/telogen or TGA state, the matrix and papilla also gradually move upward in the skin from the subdermal or lower dermal region to the upper dermal region closer to the skin surface (see FIG. 5).

There are several possible pathways through which the absorbed optical energy triggers one or both above mechanisms. Of these possible pathways, the following pathways are deemed most probable:

1. Direct absorption of light in the hair matrix damages proliferating cells and causes a complete or partial block in the hair growth. This may also trigger the internal catagen-inducing mechanisms of the follicle. This pathway is compatible with both above hypotheses.

2. Sufficient trauma is induced to blood capillaries of the dermal papilla either by direct absorption of light by the blood in these capillaries or by heat emanating from light absorbing melanocytes and other pigmented cells in the matrix. This leads to a decrease in the blood flow to the matrix and/or obstructs release of necessary substances into the matrix cells. Thus, the flow of nutrients to the proliferating hair matrix is decreased significantly, which results in deceleration of the hair growth. This pathway can involve photothermal action of light absorbed by blood in the dermal papilla and is compatible with hypothesis II.

3. Damage is caused to the companion layer of cells that move outward together with the differentiated cells of the inner root sheath (IRS). As a result, traction between the companion layer and the outer root sheath (ORS) increases and normal outward movement of the hair shaft becomes obstructed. This triggers response mechanisms in the ORS. In particular, this may influence expression of interior regulators in the ORS (e.g., inhibition of expression of the fibroblast growth factor FGF5S, which normally blocks the anagen-inhibiting activity of other regulators). As a result, transition to catagen is induced (hypothesis I above). This mechanism implies sufficient absorption of light into the hair shaft and subsequent heat transfer to the IRS, the companion layer, and (possibly) the ORS.

4. Transition of the follicle to catagen is initiated by stimulating mitotic activity of fibroblasts in the dermal papilla. The cell cycle of fibroblasts in the dermal papilla has been proposed as the principal oscillator of the hair cycle clock. Specifically, it has been postulated that the fibroblasts secrete a cocktail of "papilla morphogenes" (PM), which induce and maintain anagen only as long as these fibroblasts remain in the G0/G1 phase of the cell cycle. Once the fibroblasts enter the phase of proliferative activity, the flow of PM stops, that leading to termination of anagen. On the other hand, light has been demonstrated to stimulate proliferation of fibroblasts. This pathway suggests photochemical (with possible contribution of photothermal) action of light and supports hypothesis I.

5. As will be discussed in greater detail later, there is a very thin (less the 1 micrometer thick) basement membrane which may be considered to be part of the matrix on the side thereof adjacent the papilla. The matrix has a high concentration of melanin, generally three to ten times the concentration of melanin in the corresponding hair shaft. Damage or trauma to this basement membrane can both directly reduce proliferation activity of the matrix and indirectly interfere with this proliferation by blocking blood flow from the papilla to the matrix.

6. Trauma to the papilla can result in a reduction in the diameter and/or pigmentation of a hair shaft growing from the corresponding follicle and can also result in the follicle matrix and papilla moving upward in the skin. These changes can affect light mediated hair growth management.

Other pathways of light-induced hair growth management/temporary hair loss are also possible.

Implementation

The invention provides a new way to manage (decrease or suppress) unwanted hair growth. Light assisted hair removal is already described in the prior art. However all the devices and techniques described are designed to significantly damage or destroy the hair follicle with subsequent immediate arrest of hair growth. This kind of treatment is generally considered to be equivalent to surgical hair removal, and therefore is required to be regulated by the FDA as a medical procedure. This invention, however, provides a new treatment protocol designed not to destroy or significantly damage the hair follicle; however minor alterations are induced at the hair follicle that typically generate the specific effects on the clinical behavior of hair growth and hair attachment detailed below. These typically described effects require a specific treatment regime and/or combination with specific other methods in order to obtain the intended reduction of hair growth at a level desired by the user. These effects can be recognized by specific behavior patterns after either a single or multiple treatments with this inventive technique and are fundamentally different from the prior art for hair removal. Good cosmetic results generally do not occur immediately, but instead occur either with some delay and/or as a result of multiple treatments with short intervals, generally approximately one day to eight weeks.

Features of the invention include:

1) During the treatment, neither the hair follicle nor the hair shaft therein is destroyed.

2) The differences in clinical behavior of a typical hair follicle treated by this new method.

3) The use of multiple treatments and/or the combination of the treatment(s) with other specific methods to obtain a desired hair growth management/reduction.

4) The combination/range of parameters used.

Considering each of these features individually:

1) Usually, devices are designed to significantly damage the hair follicle, including the hair shaft itself, such prior art methods and devices generally ablating or melting the hair shaft. The fluence of many such devices is thus set to obtain ablation, or at least color change (browning), of most of the hair shafts of the hair follicles being treated. Hair shafts and hair follicles treated by the new treatment method do not typically exhibit major changes. Occasionally, some hair bending could occur. Significant browning, immediate hair shaft rupture or hair cutting, or rupture of the hair follicle itself are in general not observed with the new treatment regime. Thus, the hair shaft remains in the follicle after treatment. There is also no current intent to thermally destroy the stem cells of the hair follicle which are located at the bulge area. Structures of the hair follicle which are intended to sustain various amount of damage or trauma include the hair matrix cells, the melanocytes co-located with the hair matrix cells, the basement membrane portion of the matrix between the matrix and the papilla, the papilla cells, or other cells located close to the hair bulb including cells in the keratinozeid zone. Because the parameters used are in general less aggressive, it is possible to apply this method of treatment without prior shaving or clipping of the hairs.

2) The clinical behavior of a typical hair follicle after application of this method is generally as follows. Typically there is no immediate noticeable color change of the hair shaft or smell of burned hairs after treatment. Also, there is typically no, or at most very limited, perifollicular edema (swelling) and erythema (redness) around the treated hair follicles (this is currently a clinical endpoint of most, if not all, techniques described in the prior art). The treatment should be painless. The attachment of the hair shaft immediately after treatment is usually not significantly altered. The treated hair follicle appears to be growing normally for a period from 1 day to 6 weeks, and on average about 2 weeks, after treatment, at which time there is a significant reduction in the hair shaft's attachment to the hair follicle, permitting the hair shaft to be shed or easily removed mechanically, for example with adhesive tape. However, during the period of growth, the growth rate can be different from, normally less than, that of an untreated hair follicle, at least for most of this period, and the growth rate can also change during this period. A relatively sudden onset of hair shedding after about two weeks can be observed. Eventually the hair follicle can continue to produce a hair shaft. However this hair shaft might be less pigmented or have smaller diameter or a lower growth rate after treatment, and especially after multiple regular treatments. It can take several treatments until a change in the growth rate, diameter or pigmentation become evident.

3) Because of its clinical behavior, this method can be combined with other specific treatments; for example:

1. Painless tape stripping of loosely attached hair shafts about 1–3 weeks after treatment.

2. Multiple treatments with the intervals between treatment being scheduled or on demand, and either fixed or variable, typical intervals being from approximately one day to eight weeks/two months with treatments weekly to every three to six weeks being preferred. Other treatment intervals are also within the contemplation of the invention, the required treatment interval varying based on a number of factors including the individual being treated, the number of prior treatments, the prior treatment intervals, the treatment parameters for prior treatments, etc. For example, the treatment interval may increase as the number of treatments performed on a patient increases. One reason for this is that the follicles in anagen state have a significant matrix, and therefore, are more susceptible to the treatment. Therefore, another treatment in a week or later may be required to treat follicles which were in catagen or telogen state during the initial treatment and are now in anagen state, producing hair shafts. However, as treatments proceed, the follicles normally tend toward syncronicity, increasing the number of follicles treated during each treatment; however, the number of hair shafts may decrease as the number of treatments increases. This is one factor which can dictate the proper interval between treatments. Other parameters may also vary as the number of treatments increases. For example, because the matrix and papilla of the follicle move closer to the surface as treatments proceed, the light photons do not need to reach as deeply into the skin, permitting shorter wavelength radiation to be used, which may be more strongly absorbed by melanocytes of the matrix. The matrix being closer to the surface may also permit lower power densities to be employed for later treatments. Finally, the matrix in the foreshortened follicle is closer to other portions of the follicle, meaning that heat radiating from the matrix may also thermally traumatize additional portions of the follicle which control hair growth, for example follicular stem cells. The differences in matrix location, hair shaft diameter, pigmentation, etc. and other changes in the follicle after some number of treatments, may dictate changes in the treatment parameters for subsequent treatments which will be discussed later. Further, during a single treatment session, the radiation-applying head/device may be applied to or may pass over a given treatment area multiple times, the lack of immediate alteration or damage to the hair shaft or follicle making such multiple passes particularly feasible.

3. The new treatment method could be the only method for management of unwanted hair growth if applied sufficiently frequently (1/week up to ½ month depending on body area and patient) or this method could be used in combination with shaving, even if the rate of shaving can be reduced because of the decreased hair growth based on average hair growth rate or temporary reduction in hair density. The treatment of this invention may also result in less pseudofolliculitis barbae (PFB) after shaving if the treatment is performed immediately before, or preferably days before shaving. The primary reason for this effect is the reduction in the growth rate that in turn reduces the probability of the hair re-entry into the skin. Other contributing factors are hair miniaturization and changes in the physical/chemical structure of the hair shaft. The teachings of this invention may also be used:

a) for treatment of keratosis pilaris, this being an obstruction of the hair infundibulum by increased keratinization.

b) treatment to intentionally induce a change in hair growth stage, this being useful in clinical situations such as in cancer related chemotherapy to prevent drug related effluvium. This is because the anagen stage is the most susceptible and a shift before treatment to a different state may help decrease or prevent drug related effluvium.

c) induced hair growth synchronization may be used to condition and optimize various light assisted hair management treatments which are hair growth stage susceptible.

d) modify male beard growth to reduce frequency of required shaving.

4. The new treatment method can be combined with other hair management techniques for synergy and better cosmetic results, for example, with chemical epilation or with other lotions applied for enhanced hair growth reduction/stoppage. Such additional treatments are particularly effective after the hair shafts shed or are removed since, unlike when hair shafts are removed by plucking, waxing or similar techniques, which techniques result in edema which obstructs the infundibulum of the follicle, there is no such edema with the practice of this invention. Thus, these topical compounds more easily enter the follicle and can therefore be more effective. Therefore, the time after hair shedding may be an ideal time to apply such compounds. Soft waxing can also be used between light treatments. Internal, herbal or other natural medicines which effect hair growth management can also be used in combination with the treatments of this invention.

5. The new treatment method can be combined with additional skin treatments to enhance treatment results. For example, deep (up to the depth of the hair matrix) preheating of skin can increase the effect of the treatment. This preheating can be realized using an additional deep heating electromagnetic or acoustic device. The time of preheating can be 1–10000 seconds. A hot bath and/or hot wax can be used for the same propose. The same device as is used for treatment can also be used for preheating, but with a lower power setting. Another possible additional treatment can be massage for blood supply activation.

Treatment Parameters

The concentration of melanin and the absorption of light in the hair matrix of anagen hair next to the hair papilla, and in particular in the matrix, is 3–10 times stronger than in the hair shaft. So the temperature rise of the matrix and of this area 1 is higher than in any other portion in the hair follicle, including the hair shaft. It is therefore possible to selectively treat the hair matrix, including the basement membrane portion thereof, and the adjacent hair papilla P (see FIG. 1) without any damage to other parts of the follicle. The effect of this treatment can be a slow transition of an anagen hair follicle into the TGA or a modified phase.

Parameters

The range of parameter for the treatments of this invention has been determined for the following Tables and Figures from calculations of the Arrhenius integral A for this hottest area 1 (FIG. 1) of the hair follicle. Minimal thermal injury is defined as A=0.1 and maximal injury is A=1 (or greater); however, since the area 1 heats significantly more strongly then other areas of the follicle/hair shaft when the follicle is irradiated, even for A=1 for area 1, there is little or no damage/trauma to the remainder of the follicle/hair shaft. For a low value of A, time required to arrest hair growth should be longer.

It should be understood that the following Tables and Figures have been derived from Arrhenius computations using known process parameters (activation energy and frequency factor) for the denaturation of structural cell proteins. The mechanisms 1 through 5 involve enzyme deactivation rather than protein denaturation. The former process typically requires less energy and is initiated at lower temperatures than the latter. Therefore, the parameters below represent upper boundary estimates for power density and fluence that should be used in the practice of the present invention. It should be noted that the quantitative values of the Arrhenius parameters for the relevant processes are only known at present time with a limited accuracy. In addition, important contributions to the overall effect may be caused by non-Arrhenius-type processes (e.g., deactivation of enzymes). Therefore, the range of parameters presented here should be considered exemplary and not limiting the scope of the present invention.

Figure 2:
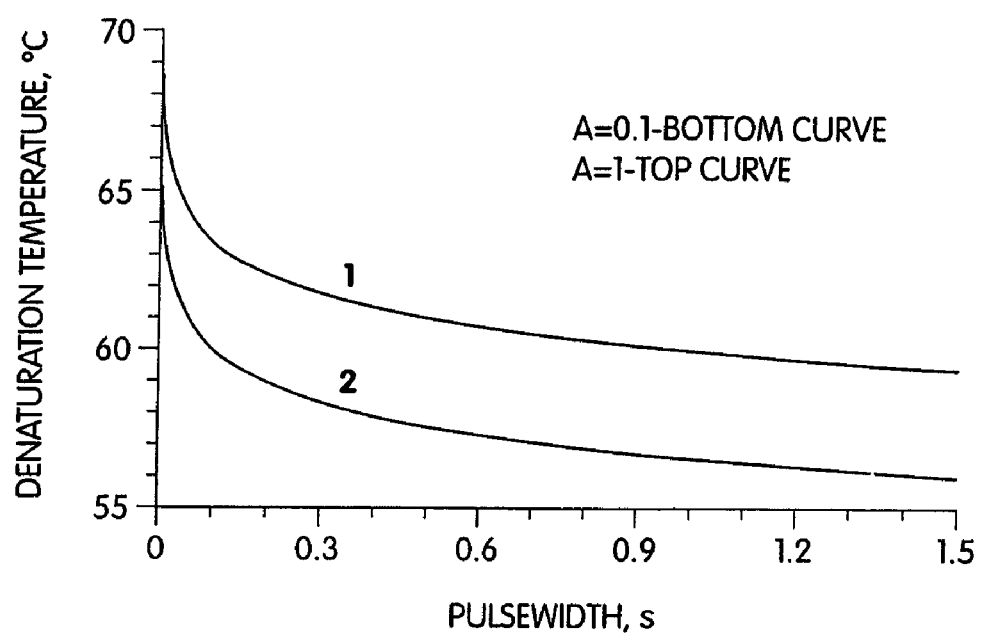
FIG. 2 is a graph illustrating preferred temperature ranges for a treated follicle matrix as a function of pulse width.

FIG. 2 shows the temperature given by the Arrhenius integral for A=0.1 (lower curve 2) and A=1 (upper curve 1). Using standard parameters of skin diffusion and thermal equations, power density and fluence needed for selective thermal injury of area 1, the hair matrix of dark/dirty blond or blonde hair, were calculated. Minimum fluence and power density were determined for dark hair and A=0.1. The light pulse used is assumed to be rectangular. Depending on the patient's hair and other factors, the temperature for a given treatment should fall between the two curves shown in FIG. 2. Another variable factor for treatment is the sub-phase of the anagen phase. In early anagen phase, the hair matrix can be close to the skin surface and more sensitive to shorter wavelengths.

TABLE 1

Range of power density W/cm$^2$ for low power photoepilation, minimum for dark hair and maximum for dark/dirty blond hair or blonde hair. The power density integrates for hair colors between those specified, and also integrates for wavelengths between those specified.

| Wavelength, | Pulsewidth, ms | | | | | | |
|---|---|---|---|---|---|---|---|
| nm | 0.1 | 1 | 10 | 100 | 1,000 | 10,000 | 100,000 |
| 600 | 2000–72000 | 210–7700 | 21–780 | 4.0–140 | 1.8–70 | 1.3–51 | 1.0–40 |
| 700 | 1500–52000 | 160–5900 | 16–600 | 3.0–110 | 1.4–53 | 1.0–39 | 0.75–30 |
| 800 | 2400–88000 | 260–9400 | 26–950 | 4.8–180 | 2.2–86 | 1.6–61 | 1.2–49 |
| 900 | 4300–160000 | 450–16000 | 45–1700 | 8.5–330 | 4.0–150 | 2.8–110 | 2.1–86 |
| 1000 | 11000–390000 | 1100–42000 | 110–4200 | 22–810 | 10–390 | 7.1–270 | 5.4–220 |
| 1100 | 10000–490000 | 1400–52000 | 140–5200 | 27–990 | 12–470 | 8.7–340 | 6.6–270 |
| 1200 | 56000–2100000 | 6000–220000 | 600–22000 | 110–4200 | 52–2000 | 36–1400 | 28–1100 |
| 600–1200 lamp | 2500–91000 | 260–9600 | 27–990 | 5.0–180 | 2.4–90 | 1.6–65 | 1.2–51 |
| 700–1200 lamp | 3400–130000 | 360–13000 | 36–1300 | 6.8–260 | 3.2–120 | 2.2–87 | 1.7–69 |

TABLE 1-continued

Range of power density W/cm² for low power photoepilation,
minimum for dark hair and maximum for dark/dirty blond hair or
blonde hair. The power density integrates for hair colors between
those specified, and also integrates for wavelengths between those specified.

| Wavelength, | Pulsewidth, ms | | | | | | |
|---|---|---|---|---|---|---|---|
| nm | 0.1 | 1 | 10 | 100 | 1,000 | 10,000 | 100,000 |
| 800–1200 lamp | 5300–200000 | 550–21000 | 56–2100 | 10–390 | 4.9–180 | 3.4–130 | 2.6–110 |

Table 1. Range of power density W/cm² for low power photoepilation, minimum for dark hair and maximum for dark/dirty blond hair or blonde hair. The power density integrates for hair colors between those specified, and also integrates for wavelengths between those specified.

TABLE 2

Range of fluence J/cm² for low power photoepilation, minimum for dark hair
and maximum for dark/dirty blonde hair or blonde hair. The fluence integrates for hair
colors between those specified, and also integrates for wavelengths between those
specified. Where the treatment involves multiple passes, the fluence given is generally
per pass, and cumulative fluence may therefore be higher for the multiple passes.

| Wavelength, | Pulsewidth, ms | | | | | | |
|---|---|---|---|---|---|---|---|
| nm | 0.1 | 1 | 10 | 100 | 1,000 | 10,000 | 100,000 |
| 600 | 0.2–7.2 | 0.21–7.7 | 0.21–7.8 | 0.40–14 | 1.8–70 | 130–510 | 100–4000 |
| 700 | 0.15–5.2 | 0.16–5.9 | 0.16–6.0 | 0.30–11 | 1.4–53 | 10–390 | 75–3000 |
| 800 | 0.24–8.8 | 0.26–9.4 | 0.26–9.5 | 0.48–18 | 2.2–86 | 16 610 | 120–4900 |
| 900 | 0.43–16 | 0.45–16 | 0.45–17 | 0.85–33 | 4–150 | 28–1100 | 210–8600 |
| 1000 | 1.1–39 | 1.10–42 | 1.2–42 | 2.2–81 | 10–390 | 71–2700 | 540–22000 |
| 1100 | 1.0–49 | 1.40–52 | 1.4–52 | 2.7–99 | 12–470 | 87–3400 | 660–27000 |
| 1200 | 5.6–210 | 6.0–220 | 6–220 | 11–420 | 52–2000 | 360–14000 | 2800–110000 |
| 600–1200 lamp | 0.25–9.1 | 0.26–9.6 | 0.27–9.9 | 0.50–18 | 2.4–90 | 16–650 | 120–5100 |
| 700–1200 lamp | 0.34–13 | 0.36–13 | 0.36–13 | 0.68–26 | 3.2–120 | 22–870 | 170–6900 |
| 800–1200 lamp | 0.53–20 | 0.55–21 | 0.56–21 | 1–39 | 4.9–180 | 34–1300 | 260–11000 |

Table 2. Range of fluence J/cm² for low power photoepilation, minimum for dark hair and maximum for dark/dirty blonde hair or blonde hair. The fluence integrates for hair colors between those specified, and also integrates for wavelengths between those specified. Where the treatment involves multiple passes, the fluence given is generally per pass, and cumulative fluence may therefore be higher for the multiple passes.

TABLE 3

Range of linear power densities (W/cm) for low power epilation by continuous
wave (CW)/continuous contact scanning (CCS) method (U.S. Pat. No. 6,273,884) as a
function of scanning speed, minimum for dark hair and maximum for dark/dirty blond or
blonde hair.

| Wavelength, | Speed of scanning, cm/sec | | | | | | |
|---|---|---|---|---|---|---|---|
| nm | 1 | 2 | 5 | 7.5 | 10 | 15 | 20 |
| 600 | 1.8–65 | 2.2–78 | 3.2–115 | 3.8–130 | 4.2–156 | 5.4–195 | 6.4–230 |
| 700 | 1.4–50 | 1.7–60 | 2.4–86 | 2.8–100 | 3.2–120 | 4–140 | 4.8–170 |
| 800 | 1.6–60 | 2–70 | 2.8–100 | 3.4–120 | 3.8–140 | 4.8–170 | 5.6–210 |
| 900 | 2.2–80 | 2.6–105 | 3.8–140 | 4.6–170 | 5.2–200 | 6.6–230 | 7.6–290 |
| 1000 | 5.4–195 | 6.4–235 | 9.4–340 | 11–415 | 13–470 | 16–600 | 19–700 |
| 1100 | 8.6–310 | 11–390 | 15–545 | 18–650 | 20–750 | 26–935 | 30–1100 |

TABLE 3-continued

Range of linear power densities (W/cm) for low power epilation by continuous wave (CW)/continuous contact scanning (CCS) method (U.S. Pat. No. 6,273,884) as a function of scanning speed, minimum for dark hair and maximum for dark/dirty blond or blonde hair.

| Wavelength, nm | Speed of scanning, cm/sec | | | | | | |
|---|---|---|---|---|---|---|---|
| | 1 | 2 | 5 | 7.5 | 10 | 15 | 20 |
| 1200 | 36–1300 | 44–1550 | 64–2350 | 76–2850 | 86–3100 | 110–3900 | 130–4700 |
| 600–1200 lamp | 1.7–62 | 2.2–75 | 3–110 | 3.6–130 | 4–155 | 5.2–180 | 6–220 |
| 700–1200 lamp | 2.2–78 | 2.6–95 | 3.8–140 | 4.6–170 | 5.2–195 | 6.6–235 | 7.6–285 |
| 800–1200 lamp | 3.4–120 | 4.2–140 | 6–220 | 7.2–260 | 8–340 | 10–365 | 12–440 |

Table 3. Range of linear power densities (W/cm) for low power epilation by continuous wave (CW)!continuous contact scanning (CCS) method (U.S. Pat. No. 6,273,884) as a function of scanning speed, minimum for dark hair and maximum for dark/dirty blond or blonde hair.

For contact scanning with a continuous wave (CW) source (for example as described in U.S. Pat. No. 6,273,884), typical temperatures and damage dynamics in the hair matrix are shown for the model of a hair bulb in FIG. 3.

Figure 3:
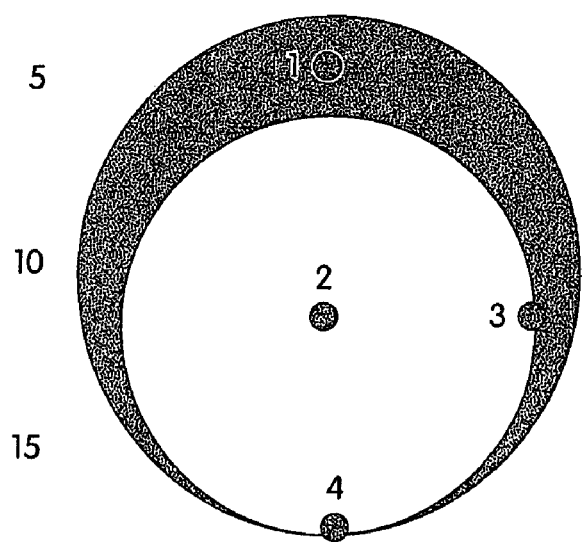
FIG. 3 is a diagrammatic representation of the matrix and papilla of a hair follicle.

In FIG. 3, the numbers have the following significance:

1. Matrix (including the basement membrane)
2. Papilla (center)
3. Papilla (right)
4. Papilla (bottom)

Figure 4:
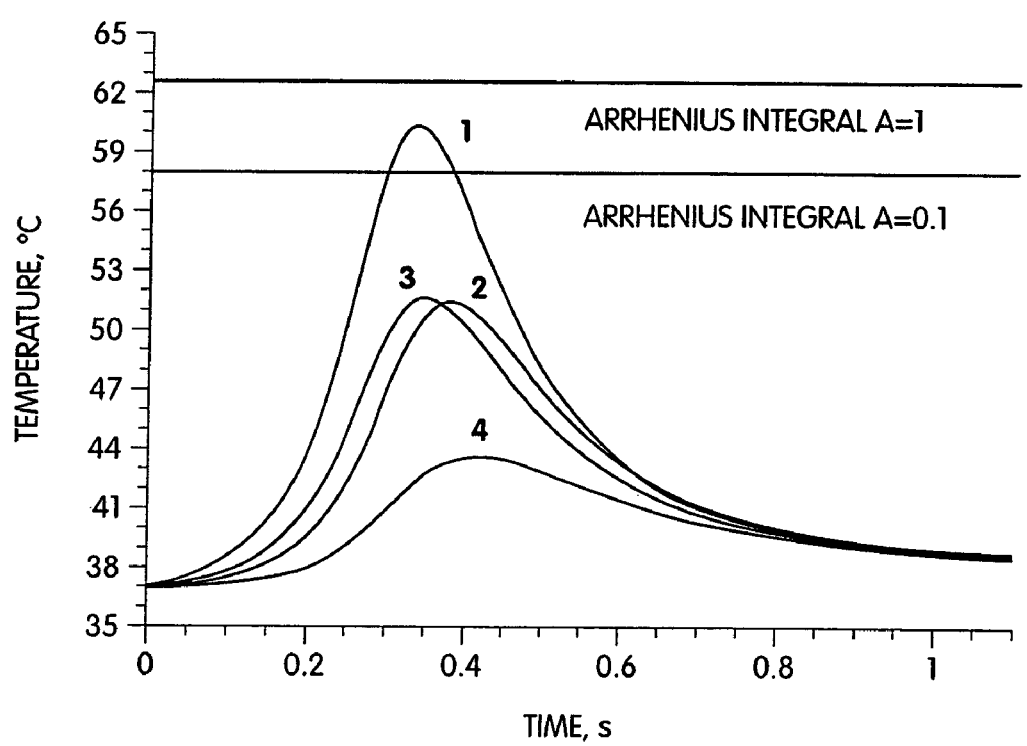
FIG. 4 is a graph of temperature as a function of time at the points in the hair follicle marked in FIG. 3.

FIG. 4 shows the temperature pulses for movement of a CW head at 30 mm/s skin type II on I-matrix/basement membrane, 2-papilla center, 3-papilla edge, 4-papilla bottom. For CW treatment, effective temperature and pulse-width depend on speed of movement of the head. For example, for movement of the CW head at 30 mm/s, a full width half maximum (FWHM) temperature pulse is 220 ms.

After several treatments, parameters lower than those specified in Tables 1, 2, 3 can be used to maintain good cosmetic results.

Figure 5:
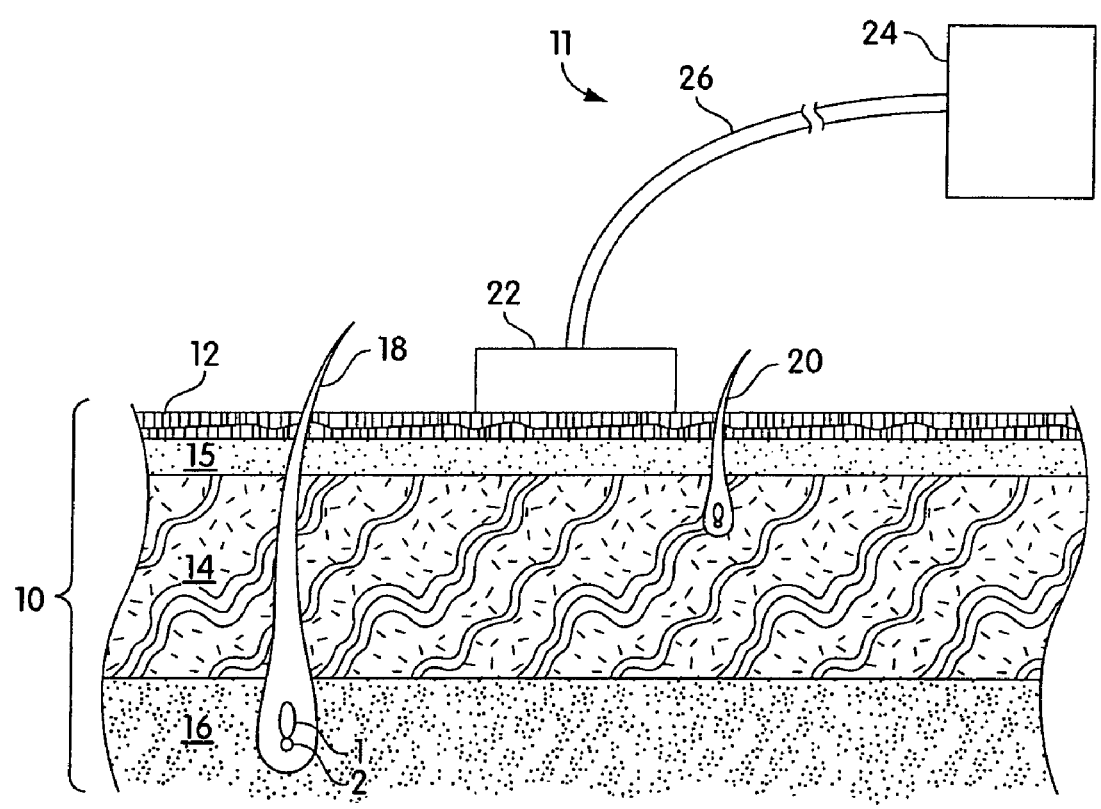
FIG. 5 is a schematic diagram of apparatus suitable for practicing the methods of this invention positioned on a skin portion.

FIG. 5 illustrates an exemplary section 10 of a patient's skin with an apparatus 11 suitable for practicing the teachings of this invention positioned thereon. Skin 10 has an epidermal layer 12 separated from an underlying dermal layer 14 by a basal layer 15, there being a subdermal layer 16 under the dermal layer. A normal hair follicle 18 in anagen state is shown with its matrix and papilla extending into subdermal layer 16, and a follicle 20 in the transitional growth arrested state is also shown, the matrix for this follicle being much higher in the dermal layer of the skin. Apparatus 11 includes a head 22 in contact with the patient's skin connected to a control box 24 by an umbilical 26. Head 22 preferably contains the radiation source, for example one or more laser diodes, LEDs, lamps or other suitable optical radiation source. Power may be provided to the source(s) from a power supply in control 24 through umbilical 26 or head 22 may contain a battery or other suitable power supply. Control electronics may also be in box 24. It is also possible for the radiation source to be in box 24, radiation from this source being applied to head 22 through the umbilical. Where the radiation source, power supply and controls can be fitted in head 22, control box 24 and umbilical 26 may be eliminated. Head 22 may move or scan over the surface of skin 10 at a selected rate, with the radiation source being a CW source or suitable pulsed source, or the source may be a pulsed source with head 22 being sequentially moved to selected treatment areas on the skin.

Where the invention is being used in a CW/CCS mode, apparatus such as that taught in U.S. Pat. No. 6,273,884 may be utilized in practicing the teachings of the invention, the apparatus being operated with the power densities and other parameters specified herein. GaAs or other diode lasers, laser bars, LEDs, fiber lasers, gas discharged Xe or Kr lamps, halogen and tungsten lamps with proper color temperature and filtering, other lamps or other suitable light sources can be used as light sources. Where the invention is being operated in pulse mode, a variety of optical dermatology apparatus, either utilizing a coherent/laser source, LED, incoherent/lamp or other suitable optical radiation source, may be utilized. Since for this method of treatment, both low cost and efficacy of the source used are very important, preferable light sources are diode lasers or laser bars, LEDs, fiber lasers, gas discharge lamps, and halogen or tungsten lamps with proper color temperature and filtering. Gas discharge and tungsten lamps can be linear, circular, U-shaped, etc. The color temperature of a lamp can in the range 2500–6000° K. and can be increased by the use of short arc lamps. For example, a short arc xenon lamp can be packaged in ceramic-to-metal construction integrated with a reflector. Regardless of the apparatus utilized, it needs to be operated in the power density and other parameter ranges taught above. Because of the relatively low power densities required by this invention, a relatively small, light, inexpensive and safe radiation source can generally be employed.

While the invention has been described above with respect to preferred embodiments, these are being provided by way of illustration only, and the methods described, the apparatus and the treatment parameters may vary depending on patient, the treatment being performed and other factors. Such variations, as well as other variations in form and detail, would be apparent to one ordinarily skilled in the art. Thus, the invention is to be limited only by the appended claims.

What is claimed is:

1. A method for hair growth management in a treatment area of a patient's skin including:
    applying a first dose of optical radiation from a source to hair follicles in said treatment area with a first set of treatment parameters comprising a wavelength, power density and duration sufficient to at least modify a matrix portion of the follicles, and
    applying a second dose of optical radiation at at least one subsequent selected time interval with a second set of treatment parameters, wherein the second set of treatment parameters comprises shorter wavelengths and lower power densities than the first set of treatment parameters
wherein at least the second treatment parameters are selected based on hair color.

2. A method as claimed in claim 1 wherein each follicle matrix includes a basement membrane between the matrix and papilla of the follicle, and wherein the basement membrane of the follicle is traumatized.

3. A method as claimed in claim 1 wherein said matrix of each follicle being treated is heated to a temperature between about 55° C. and about 70° C., but at least most of each such follicle is at a temperature below said range.

4. A method as claimed in claim 1 including the step of repeating the first and second application steps at selected time intervals.

5. A method as claimed in claim 4 wherein said selected time intervals range is from approximately one day to eight weeks.

6. A method as claimed in claim 4 wherein said selected time intervals range is from approximately one week to six weeks.

7. A method as claimed in claim 1 including the step of stripping loose hairs from the treatment area at a time approximately one to two weeks after the method is performed.

8. The method as claimed in claim 7, wherein said stripping step comprises using a tape to remove loose hairs from the treatment area.

9. The method as claimed in claim 1, wherein the method further includes the step of scanning optical radiation from said source over said treatment area at a scanning speed between 1–20 cm/sec, such that the power densities of radiation from said source are selected based on the wavelength of the source, the width of the scanning beam and the scanning speed.

10. A method as claimed in claim 9, wherein said optical radiation is from a continuous wave radiation source.

11. A method as claimed in claim 1 wherein at least selected portions of said treatment area are irradiated a plurality of times during a treatment.

12. A method for hair growth management in a treatment area of a patient's skin including:
applying a first dose of optical radiation to hair follicles in said treatment area with a first set of treatment parameters comprising a wavelength, power density and duration sufficient to modify a matrix portion of the follicles,
applying a second dose of optical radiation at at least one subsequent selected time interval with a second set of treatment parameters, wherein the second set of treatment parameters comprises shorter wavelengths and lower power densities than the first set of treatment parameters; and
repeating said applying steps at selected time intervals,
wherein the treatment parameters are selected based on hair color.

* * * * *